(12) United States Patent
Biedermann et al.

(10) Patent No.: US 9,192,417 B2
(45) Date of Patent: Nov. 24, 2015

(54) MONOPLANAR BONE ANCHORING DEVICE WITH SELECTABLE PIVOT PLANE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 186 days.

(21) Appl. No.: 13/712,942

(22) Filed: Dec. 12, 2012

(65) Prior Publication Data

US 2013/0150904 A1 Jun. 13, 2013

Related U.S. Application Data

(60) Provisional application No. 61/569,915, filed on Dec. 13, 2011.

(30) Foreign Application Priority Data

Dec. 13, 2011 (EP) .................................. 11193326

(51) Int. Cl.
*A61B 17/84* (2006.01)
*A61B 17/70* (2006.01)
*A61B 19/00* (2006.01)

(52) U.S. Cl.
CPC ............. *A61B 17/84* (2013.01); *A61B 17/7035* (2013.01); *A61B 17/7038* (2013.01); *A61B 2019/307* (2013.01)

(58) Field of Classification Search
CPC . A61B 17/84; A61B 17/7035; A61B 17/7038
USPC ................. 606/70, 71, 246–279, 280–299
See application file for complete search history.

(56) References Cited

U.S. PATENT DOCUMENTS

| | | | |
|---|---|---|---|
| 7,749,258 B2 | 7/2010 | Biedermann et al. | |
| 7,766,944 B2 | 8/2010 | Metz-Stavenhagen | |
| 7,951,172 B2 | 5/2011 | Chao et al. | |
| 2006/0155277 A1* | 7/2006 | Metz-Stavenhagen | 606/61 |
| 2008/0306526 A1 | 12/2008 | Winslow et al. | |
| 2009/0216280 A1* | 8/2009 | Hutchinson | 606/279 |
| 2010/0198273 A1* | 8/2010 | Kwak et al. | 606/308 |
| 2010/0305621 A1 | 12/2010 | Wang et al. | |
| 2011/0040335 A1 | 2/2011 | Stihl et al. | |
| 2011/0178559 A1 | 7/2011 | Barry | |
| 2011/0218578 A1* | 9/2011 | Jackson | 606/305 |

* cited by examiner

*Primary Examiner* — Christopher Beccia
(74) *Attorney, Agent, or Firm* — Christie, Parker & Hale, LLP

(57) ABSTRACT

A bone anchoring device is provided including a receiving part for receiving a rod, the receiving part having a longitudinal axis, a first bore coaxial with the longitudinal axis and a second bore; an anchoring element having a first end for insertion into a bone and a second end positionable within the second bore, the second end including a head. The anchoring element is movable relative to the receiving part in a limited angular range about the longitudinal axis, the angular range lying in a single plane. The bone anchoring device further includes a guiding member configured to rotate in the first bore, wherein the head of the anchoring element is connected to the guiding member and wherein a form-fit connection between the head and the guiding member limits the movement of the anchoring element to the single plane. A first locking element acts on the guiding member to fix the rotational position of the guiding member and a second locking element acts on the head to fix the head relative to the receiving part.

16 Claims, 8 Drawing Sheets

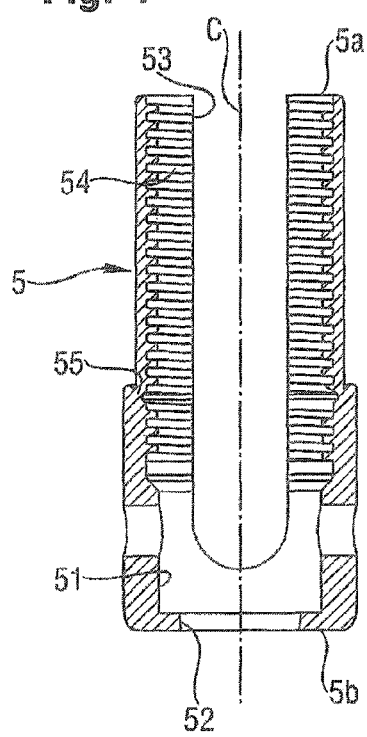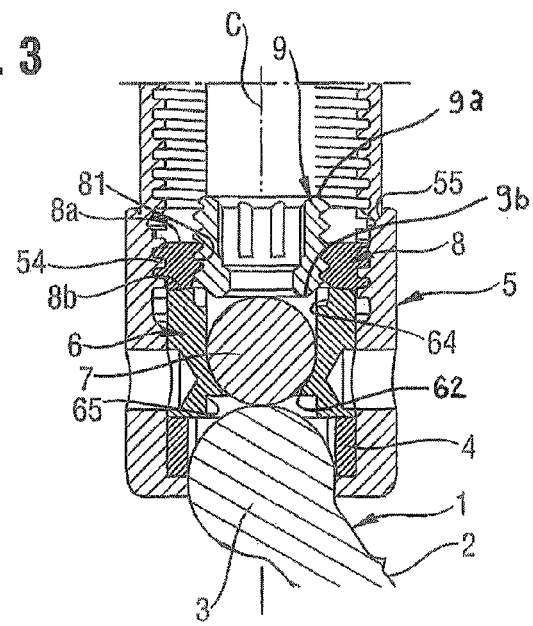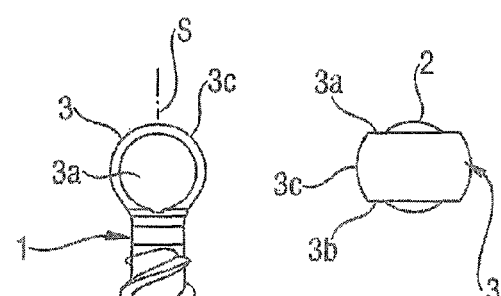

MONOPLANAR BONE ANCHORING DEVICE WITH SELECTABLE PIVOT PLANE

CROSS-REFERENCE TO RELATED APPLICATIONS

The present disclosure claims the benefit of U.S. Provisional Patent Application Ser. No. 61/569,915, filed Dec. 13, 2011, the contents of which are hereby incorporated by reference in their entirety, and claims priority from European Patent Application EP11193326.3, filed Dec. 13, 2011, the contents of which are hereby incorporated by reference in their entirety.

BACKGROUND

1. Field of the Invention

The present disclosure relates to a bone anchoring device, and more particularly to a monoplanar bone anchoring device with a selectable pivot plane. The bone anchoring device comprises a receiving part for receiving a rod, an anchoring element having a first end for insertion into the bone or into a vertebra and a second end including a head, wherein the anchoring element is movable relative to the receiving part in a limited angular range about the longitudinal axis, the angular range lying in a single plane. The bone anchoring device further comprises a guiding member configured to rotate in the receiving part, wherein a form-fit connection between the guiding member and the anchoring element limits the movement of the anchoring element to the single plane and wherein the single plane can be selected by rotating the guiding member. The orientation of the pivot plane is fixed by a first locking element that acts onto the guiding member and the angular position of the bone anchoring element is locked by a second locking element that also fixes the rod.

2. Description of Related Art

U.S. Pat. No. 7,749,258 B2 describes a bone anchoring device including a receiving part for receiving a rod and an anchoring element being movable relative to the receiving part in a limited angular range about the longitudinal axis of the receiving part, wherein the angles are lying in a single plane.

U.S. Pat. No. 7,951,172 B2 describes a bone screw assembly including an anchor portion and a head portion, such as a rod-receiving portion, movably mounted to the anchor portion to allow for controlled angulation between the anchor portion and the head portion. The anchor portion is pivotable in one or more selected directions about an axis relative to the head portion. A restriction member prevents the anchor portion from pivoting in one or more different directions about another axis relative to the head portion and/or spinal fixation element received in the head portion. The restriction member may also serve as a compression member and/or rod seat for seating a spinal rod coupled to the bone screw assembly.

The bone anchoring devices described above all have one or more defined positions relative to the rod in which the shank can be pivoted in a single plane.

U.S. Pat. No. 7,766,944 B2 describes an anchoring element for fastening a rod of a device for adjusting a human vertebral column on a vertebra and having a retainer-receiving a rod, a securing element attachable on the retainer and acting against the rod, a fastening element for attachment to the vertebral body and a clamping device between the retainer and the fastening element including a ring-shaped mount, a partially spherical bearing and an intermediate element embedded in the mount and surrounding the bearing. The bearing comprises level guiding surfaces on opposite sides. The intermediate element has mating counter surfaces which enable the retainer to move in one axial direction only relative to the fastening element.

SUMMARY

It is an object of embodiments of the invention to provide an improved bone anchoring device that can be used in an increased variety of applications and that provides for a comfortable handling.

An embodiment of the bone anchoring device allows the position of the single pivot plane to be selected from a range of 360° about the longitudinal axis of the receiving part. Therefore, a plane can be selected, whether the single plane contains the rod axis or is, for example, perpendicular to the rod axis or includes any other specific angle with the rod axis. The plane is adjustable by rotating the receiving part with respect to the bone anchoring element. Once the pivot plane has been fixed, the bone anchoring element can pivot relative to the receiving part in that plane only.

In one embodiment, the guiding member and the bone anchoring element can be locked independently.

In another specific embodiment, the pivot angle of the bone anchoring element in the selected pivot plane is enlarged to one side compared to the other side with respect to the longitudinal axis of the receiving part. This renders the bone anchoring device particularly suitable for the application of lateral mass fixation, for example, for the cervical spine.

BRIEF DESCRIPTION OF THE DRAWINGS

Further features and advantages will become apparent and will be best understood by reference to the following detailed description reviewed in conjunction with the accompanying drawings. In the drawings:

FIG. 3 shows a cross-sectional view of the bone anchoring device of FIG. 2, the cross-section taken perpendicular to the rod axis.

FIG. 4 shows a cross-sectional view of the receiving part of the bone anchoring device according to the first embodiment, the cross-section taken perpendicular to a longitudinal axis of a channel for receiving the rod.

FIG. 5 shows a side view of the bone anchoring element.

FIG. 6 shows a top view of the bone anchoring element.

DETAILED DESCRIPTION

Figure 1:
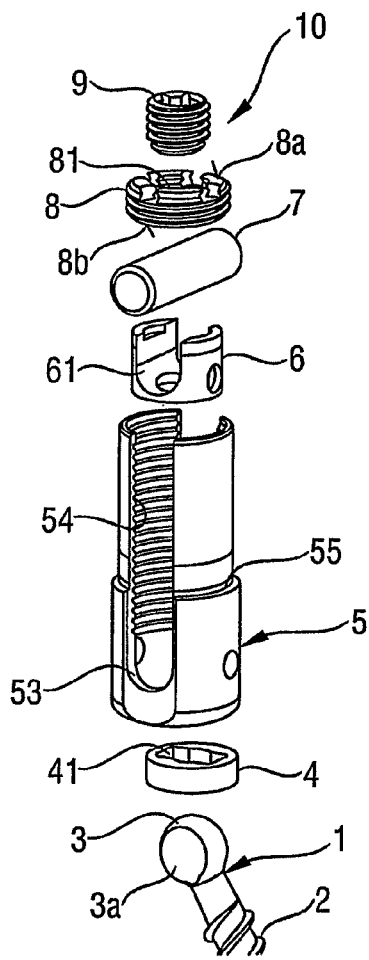
FIG. 1 shows a perspective exploded view of the bone anchoring device according to a first embodiment of the present disclosure.
Figure 2:
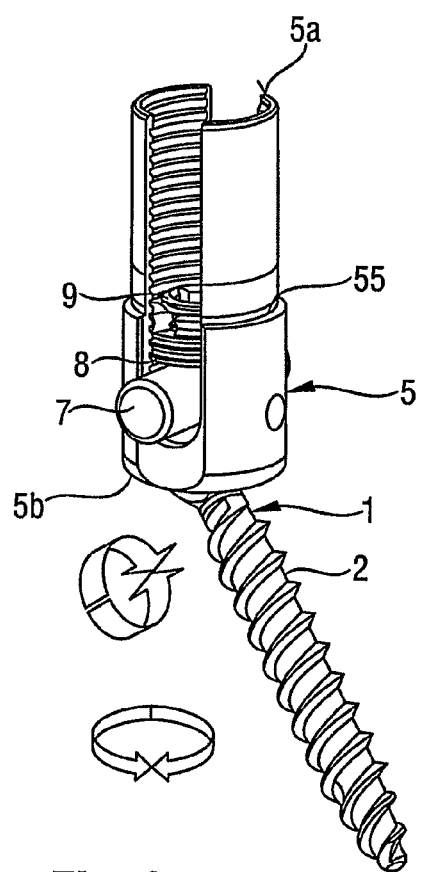
FIG. 2 shows a perspective view of the bone anchoring device of FIG. 1 in an assembled state.
Figure 7:
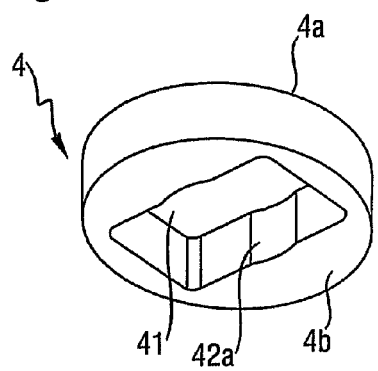
FIG. 7 shows a perspective view of a guiding member connectable to the bone anchoring element.
Figure 8:
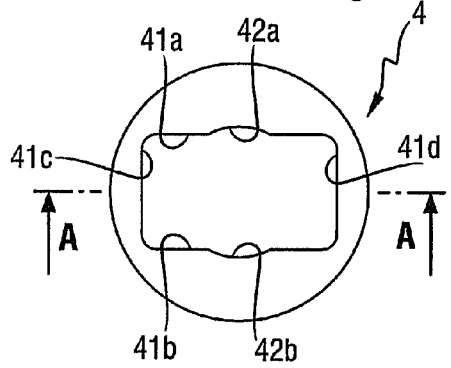
FIG. 8 shows a top view of the guiding member.
Figure 9:
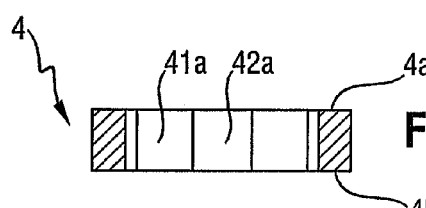
FIG. 9 shows a cross-sectional view of the guiding member, the section taken along line A-A in FIG. 8.
Figure 10:
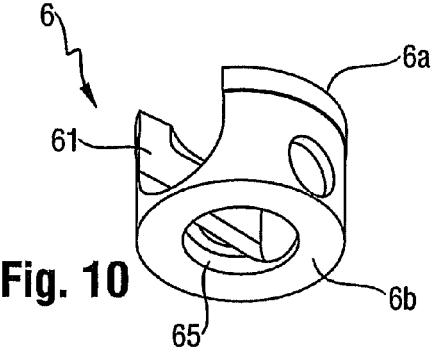
FIG. 10 shows a perspective view of the pressure member of the bone anchoring device.

As shown in FIGS. 1 to 3, the bone anchoring device according to a first embodiment includes a bone anchoring element 1 in the form of bone screw having a shank 2 with a threaded portion and a head 3. The head 3 is guided in a guiding member 4 provided in a receiving part 5. The receiving part 5 couples the bone anchoring element 1 to a stabilization rod 7. A pressure member 6 is arranged between the guiding member 4 and the rod 7. Furthermore, a locking device 10 comprising a first locking element 8 for fixing the guiding member 4 and a second locking element 9 for securing and fixing the rod 7 and for locking the head 3 is provided.

As shown in FIGS. 5 and 6, the head 3 of the bone anchoring element 1 is shaped substantially as a segment of a sphere including a largest diameter of the sphere, the segment being oriented with its rotational axis perpendicular to the shank axis S. The head 3 comprises two opposite flat surfaces 3a, 3b that extend substantially parallel to each other and parallel to the shank axis S and a spherical portion 3c.

As shown in FIGS. 3 and 4, the receiving part 5 has a first end 5a and an opposite second end 5b. A first bore 51 extends from the first end 5a to a distance from the second end 5b. The first bore 51 defines an axis of symmetry C extending through the first end 5a and the second end 5b. At the second end 5b, there is a second bore 52 with a diameter smaller than the diameter of the first bore 51. The second bore 52 is in communication with the first bore 51. Adjacent to the first end 5a, a substantially U-shaped recess 53 is provided that forms a channel for receiving the rod 7. By means of the recess 53, two free legs are formed that are provided with an internal thread 54 that works in combination with the first locking element 8. The depicted embodiment shows the receiving part 5 for a longhead bone anchoring device comprising extended legs. A predetermined breaking point 55 is located at a distance from the first end and can break off from the remaining receiving part 5, severing the portion between the first end 5a and the predetermined breaking point 55. Such a longhead receiving part may be used, for example, for minimally invasive surgery. It shall be noted that the receiving part 5 may also be designed without the longhead, the first end 5a then being approximately at the predetermined breaking point 55.

As depicted in FIGS. 3 and 7 to 9, the guiding member 4 is a substantially cylindrical part that has an outer diameter permitting it to be introduced into the first bore 51 and resting at the transition between the first bore 51 and the second bore 52, as shown in FIGS. 3 and 4. The guiding member 4 comprises a first end 4a, an opposite second end 4b and a substantially rectangular recess 41 extending through the guiding member 4 from the first end 4a to the second end 4b. The recess 41 has long side walls 41a, 41b with a length that substantially corresponds to or is slightly larger than the diameter of the spherical portion 3c of the head 3. The short side walls 41c, 41d each have a length that substantially corresponds or is slightly larger than the thickness of the head 3 between the opposite flat surfaces 3a, 3b. Hence, the head 3 fits into the recess 41. When the head 3 is inserted in the recess 41, the long sidewalls of the recess 41 extend along the flat surfaces 3a, 3b of the head 3. At substantially the center of the long side walls 41a, 41b, two opposite cylindrical or curved recesses 42a, 42b are provided that extend in an axial direction relative to the cylindrical guiding member 4 so that there is a space between the head 3 and the guiding member 4 when the head 3 is inserted. The space allows access for a tool to engage the flat surfaces 3a, 3b of the head 3 in order to rotate the bone anchoring element 1.

As shown in FIG. 3, the height of the guiding member 4 is such that when the head 3 is inserted, a portion of the head 3 projects out of the first end 4a of the guiding member 4.

Figure 11:
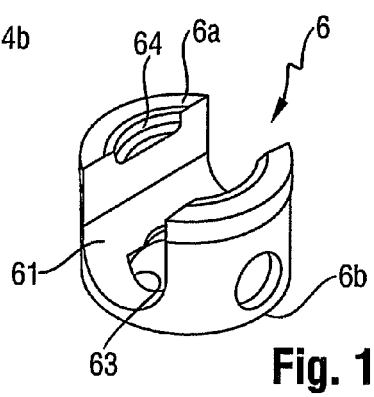
FIG. 11 shows another perspective view of the pressure member.
Figure 12:
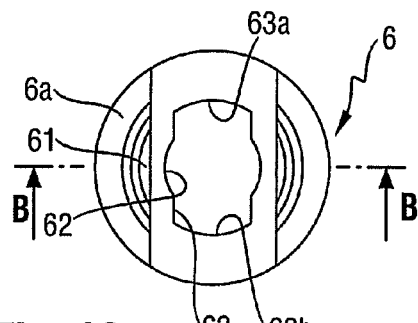
FIG. 12 shows a top view of the pressure member.
Figure 13:
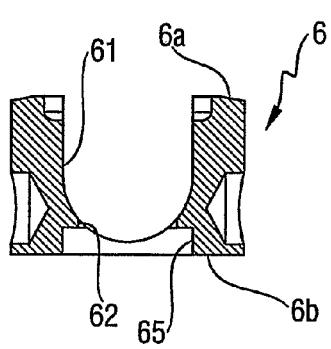
FIG. 13 shows a cross-sectional view of the pressure member, the cross-section taken along line B-B in FIG. 12.

Referring to FIGS. 10 to 13, the pressure member 6 is a substantially cylindrical part having a first end 6a and an opposite second end 6b. The size of the pressure member 6 is such that the pressure member 6 can be inserted into the receiving part 5 and moved therein in an axial direction. The first end 6a faces the first end 5a of the receiving part 5 and the second end 6b faces the guiding member 4. Adjacent the first end 6a, a substantially U-shaped recess 61 is provided that has a depth such that the first end 6a ends at a position above the rod surface when the rod 7 rests on the bottom of the recess 61. The first end 6a has a bevelled surface with an incline such that the height of the pressure member 6 is slightly decreasing towards the outer circumference, as can be seen in FIGS. 3 and 13. With reference to FIG. 12, a circular through-hole 62 extends from the bottom of the recess 61 to the second end 6b. The diameter of the through-hole 62 is smaller than the diameter of the rod 7. In addition, as can be seen in particular in FIGS. 12 and 13, a substantially rectangular recess 63 with two opposite sides 63a, 63b, that are curved outwards along the circumference of hole 65 is provided at the bottom of the U-shaped recess 61 with the long sides of the rectangle oriented along the rod axis. The length of the substantially rectangular recess 63 is greater than the diameter of the through-hole 62. By means of this structure, a portion of the rod 7 can extend into the recess 63. At the second end 6b, a hole 65 is provided that permits a portion of the head 3 to extend into the hole 65, when the bone anchoring device is assembled, as depicted in FIG. 3. As a result, the rod 7 presses with its lower side directly onto the head 3. The pressure member 6 acts with its second end 6b directly onto the guiding member 4 without touching the head 3 of the bone anchoring element 1.

The pressure member 6 further comprises a coaxial recess 64 at the first end 6a that has a diameter greater than the diameter of the second locking element 9, as shown in FIG. 11.

Referring to FIGS. 1 to 3, the locking device will be described. The first locking element 8 of the locking device 10 is a screw with a first end 8a and an opposite second end 8b with an external thread that works in combination with the internal thread 54 on the receiving part 5. The thread may have a thread form to prevent splaying of the legs formed by the channel in the receiving part 5. Such a thread form may be, for example, a flat thread, as depicted in FIG. 3. At the first end 8a, there may be an engagement structure, such as for engagement with a screwdriver. The second end 8b of the first locking element may be bevelled corresponding to the bevelled portion of the first end 6a of the pressure member 6 as depicted in FIG. 3. The first locking element 8 further comprises a threaded through-hole 81 for receiving the second locking element 9. The thread form may be any thread form, for example, a metric thread. The second locking element 9 is shown as a set screw having a first end 9a and a second end 9b. The second end 9b is configured to act onto the rod 9. The size of the locking device 10 is such that when the first locking element 8 and the second locking element 9 are tightened, the first locking element 8 and the second locking element 9 do not substantially project over the predetermined breaking point 55 of the receiving part 5.

In the assembled state as shown in FIGS. 2 and 3, the first locking element 8 is configured to act onto the pressure member 6 only. The pressure member 6 is configured to act onto the guiding member 4 only. The second locking element 9 extends with its second end 9b into the coaxial recess 64 provided in the pressure member 6. By means of this, the second locking element 9 is not in contact with the pressure member 6.

In the assembled state, the pressure member 6 is arranged in an aligned position, in which the substantially U-shaped recess 61 is aligned with the substantially U-shaped recess 53 of the receiving part 5. The pressure member 6 may be held provisionally in this position, for example, by crimping.

The bone anchoring device as a whole or in parts is made of a bio-compatible material, such as a bio-compatible metal, for example titanium, stainless steel, a bio-compatible alloy, such as Nitinol, or of bio-compatible plastic materials, such as, for example, polyetheretherketone (PEEK).

In use, the bone anchoring device may be pre-assembled, such that the bone anchoring element 1 with the guiding member 4 is held in the receiving part 5 and the pressure member 6 is inserted and aligned. The bone anchoring element 1 is then screwed into the bone or in a vertebra by engaging the flat surfaces 3a, 3b of the head with a tool. Because the head 3 is connected to the guiding member 4 in a form-fit manner, the guiding member 4 rotates during the screwing-in operation. By rotating the guiding member 4, the plane in which the bone anchoring element 1 can pivot relative to the receiving part 5, is defined. The position of the guiding member 4 relative to the receiving part 5 that defines the pivot plane, can be maintained, if the pressure member 6 is held in a preliminary position by means of crimping so that the pressure member 6 can exert a biasing force onto the guiding member 4 that holds the relative position between the receiving part 5 and the guiding member 4.

After at least two bone anchoring devices are inserted into bone parts or adjacent vertebrae, the receiving parts 5 are pivoted in the single plane defined by the position of the guiding member 4, so that they are aligned to permit the insertion of the rod 7. Thereafter, the locking device 10 is inserted. By tightening the first locking element 8, pressure is exerted onto the first end 6a of the pressure member 6 and with the pressure member 6 onto the guiding member 4. By means of this, the pivot plane for the bone anchoring element 1 is fixed. Then, the second locking element 9 is tightened until its second end 9b presses onto the rod 7, which in turn presses onto the head 3, as shown in FIG. 3, until the angular position of the bone anchoring element 1 in the pivot plane is locked. By loosening the second locking element 9, further adjustments of the rod 7 and of the angular position of the bone anchoring element 1 in the pivot plane can be made, while the orientation of the pivot plane remains fixed.

Figure 14:
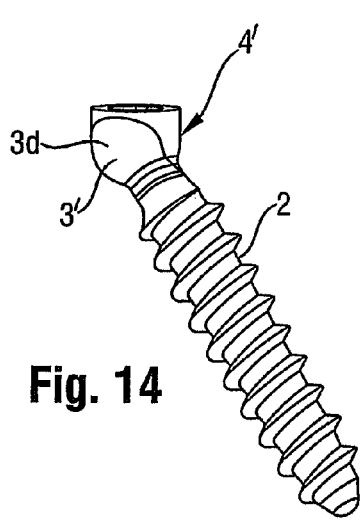
FIG. 14 shows a perspective view of a bone anchoring element with a modified guiding member.
Figure 15:
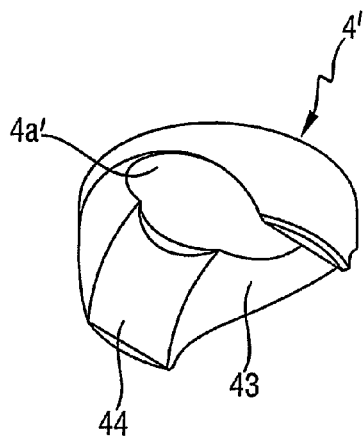
FIG. 15 shows a perspective view of the modified guiding member shown in FIG. 14.

Further modifications are conceivable. For example, as shown in FIGS. 14 and 15, the single pivot plane may be defined by the combination of a head 3' that has a spherical portion 3d and central cylindrical portion (not shown) with the cylinder axis perpendicular to the screw axis. The head 3' operates with a guiding member 4' that has a corresponding spherical portion 43 and a corresponding cylindrical portion 44 and a recess 4a' for passing through a portion of the head 3'.

Figure 16:
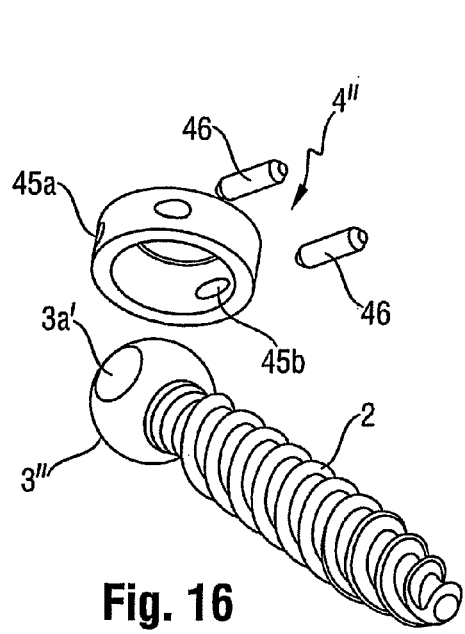
FIG. 16 shows a perspective exploded view of a bone anchoring element and another modified guiding member.
Figure 17:
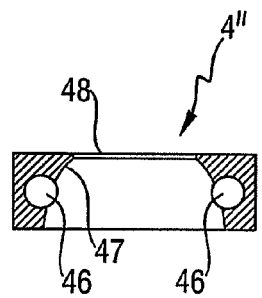
FIG. 17 shows a cross-sectional view of the guiding member shown in FIG. 16, the cross-section taken along the central axis.

In a further modification shown in FIGS. 16 and 17, the head 3" has two opposite flat surfaces 3a', 3b' that are smaller than in the first embodiment. The guiding member 4" is a substantially cylindrical ring with two bores 45a, 45b that are on opposite sides of the ring for receiving pins 46. Inside the ring has a substantially dome-shaped surface 47 with a central hole 48. When the pins 46 are inserted into the bores 45a, 45b, they limit the rotation of the screw head 3" within the guiding member 4" so that the bone anchoring element 1 can pivot only in one single plane.

Figures 18, 19:
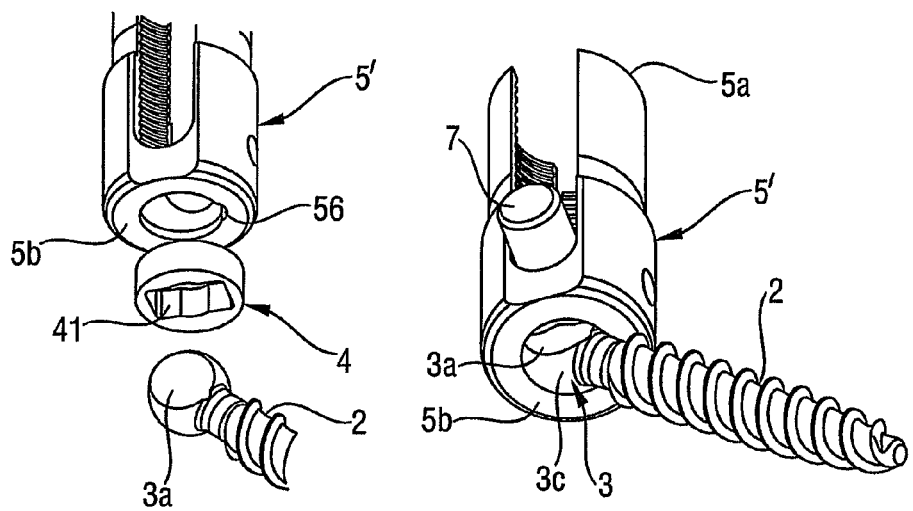
FIG. 18 shows a perspective exploded view of a second embodiment of the bone anchoring device.
FIG. 19 shows a perspective view of the second embodiment of the bone anchoring device.
Figure 20:
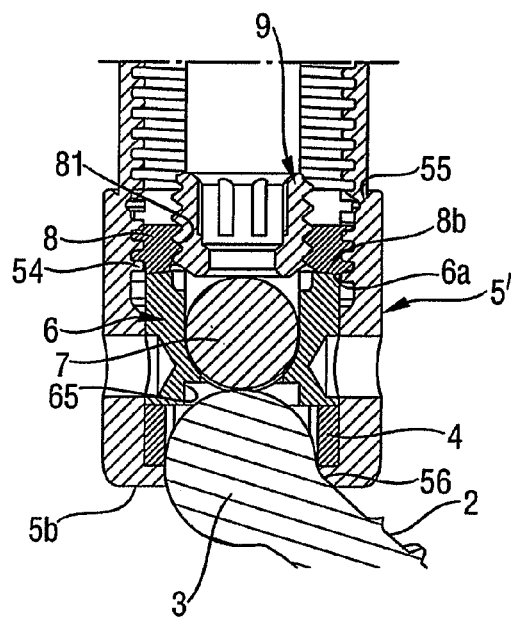
FIG. 20 shows a cross-sectional view of the bone anchoring device according to the second embodiment, wherein the cross-section has been taken perpendicular to the rod axis.

FIGS. 18 to 20 show a second embodiment of the bone anchoring device. This embodiment differs from the bone anchoring device according to the first embodiment only in the design of the receiving part 5'. All other parts and portions are the same and the description thereof will not be repeated. The bone anchoring device has a preferential orientation for the pivot plane.

The receiving part 5' has at its second end 5b a countersunk area 56, that allows the bone anchoring element 1 to be pivoted at a larger angle when the pivot plane is oriented such that the bone anchoring element 1 extends through the countersunk area 56. Hence, the second end 5b defines an edge bounding the second bore 52 that is asymmetric in the single pivot plane. As shown in FIG. 20, when the bone anchoring element 1 is pivoted into the countersunk area 56, the maximum pivot angle is larger than in a direction opposite to countersunk area 56.

The bone anchoring device according to the second embodiment can be used as bone anchoring device without an enlarged pivot angle at a specific location, when the rectangular recess 41 of the guiding member 4 is not aligned with the countersunk area 56. It can be also used as bone anchoring device with an enlarged pivot angle, when the pivot plane is aligned with the countersunk area 56.

The bone anchoring device according to the second embodiment may also be modified. For example, the bone anchoring element 1 and the guiding member 4 may be designed as the bone anchoring element 1 and the guiding member 4 according to FIGS. 14 to 17.

Figure 21:
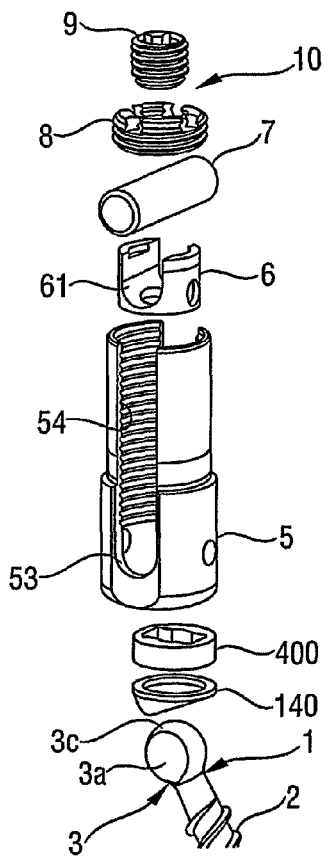
FIG. 21 shows a perspective exploded view of a bone anchoring device according to a third embodiment.
Figure 22:
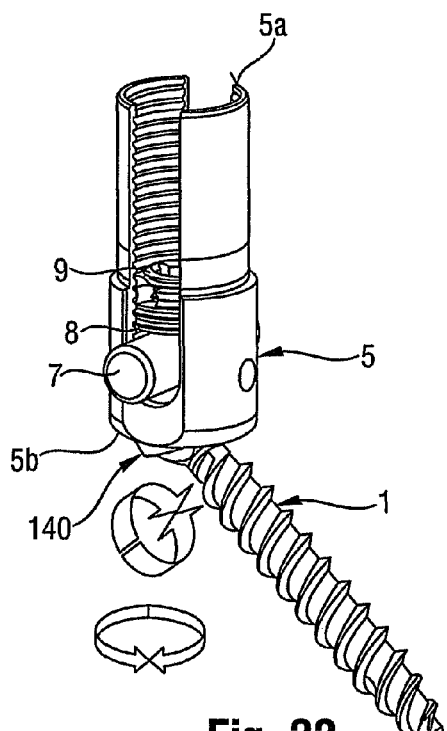
FIG. 22 shows a perspective view of the bone anchoring device of FIG. 21 in an assembled state.

With reference to FIGS. 21 and 22, a third embodiment of the bone anchoring device will be described. The bone anchoring device according to the third embodiment differs from the bone anchoring device according to the first embodiment by the guiding member 400 and by an additional seat member 140. All other parts are the same as in the first embodiment and the description thereof shall not be repeated. The guiding member 400 according to the third embodiment is substantially identical to the guiding member 4, however, has a smaller height in the axial direction.

Figure 23:
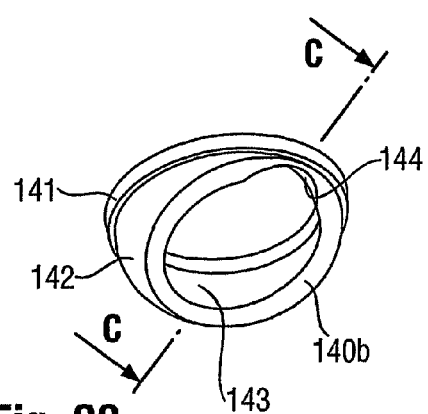
FIG. 23 shows a perspective view of a seat member of the bone anchoring device of FIG. 21.
Figure 24:
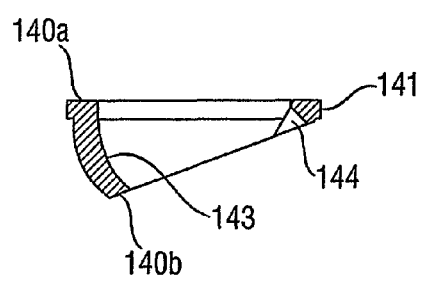
FIG. 24 shows a cross-section view of the seat member of FIG. 23, the cross-section taken along line C-C in FIG. 23.

A seat member 140 is provided that has a first end 140a and a second end 140b and a substantially hollow cylindrical portion 141 adjacent the first end 140a. The hollow cylindrical portion 141 has an outer diameter that is only slightly smaller than the inner diameter of the first bore 51, so that the first portion 141 may rest at a transition between the first bore 51 and the second bore 52. The inner diameter of the first portion 141 is smaller than the largest diameter of the head 3 and larger than the diameter of the shank 2. The seat member 140 further comprises a second portion 142 that has a substantially spherical inner surface 143 for providing a seat for the head 3. The outer surface is spherical, but can also have another shape. The size of the second portion 142 is such that the second portion 142 can extend at least partially through the second bore 52. As depicted in FIGS. 23 and 24, the second portion 142 has an inclined lower edge forming the second end 140b that is inclined relative to the plane defined by the second end 5b of the receiving part 5. When the seat member 140 is inserted into the receiving part 5, the second end 140b defines an edge bounding the second bore 52. The opening defined by the inclined lower edge has a diameter smaller than the diameter of the head 3 and larger than the diameter of the shank 2. At a position closest to the first portion 141 there is a recess 144 in the area of the edge that is shaped corresponding to the spherical portion 3c of the head 3. The head 3 thus can extend into the recess 144 to further enlarge the maximum pivot angle. The recess 144 of the seat member also provides a form-fit connection to the head 3.

Figure 25:
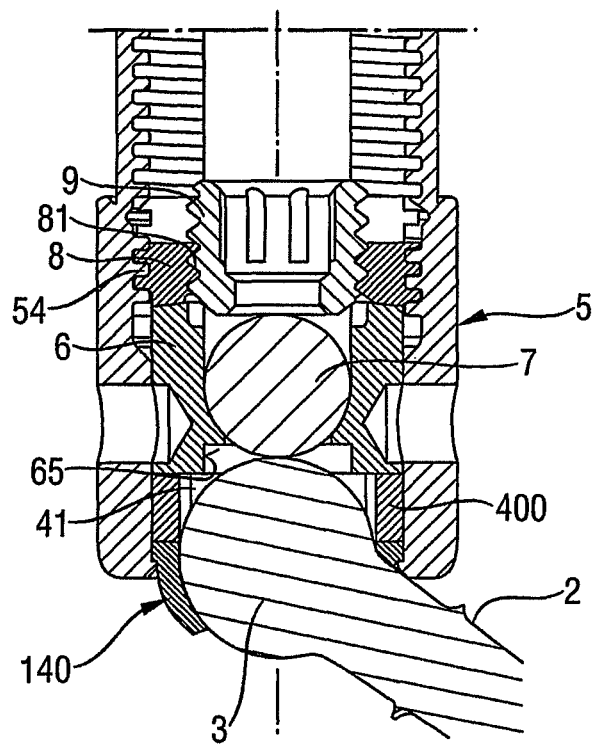
FIG. 25 shows a cross-sectional view of the bone anchoring device according to FIG. 22, the cross-section taken perpendicular to the rod axis.
Figure 26:
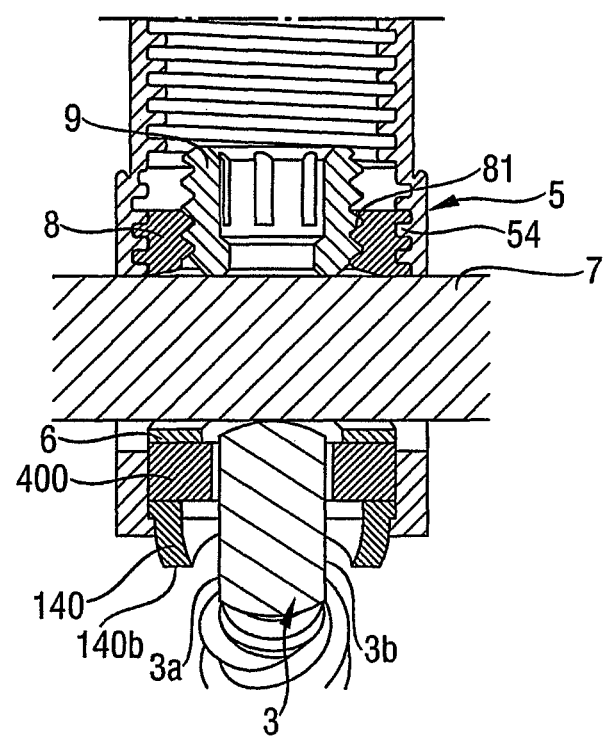
FIG. 26 shows a cross-sectional view of the bone anchoring device of FIG. 22, the cross-section taken along the rod axis.

When the seat member 140 is inserted into the receiving part 5, the second portion 142 extends through the second bore 52. When the bone anchoring element 1 is held in the seat member 140 and is coupled to the guiding member 400, the seat member 140 and the guiding member 400 are rotatable together with the bone anchoring element 1 with respect to the receiving part 5. The seat member 140 defines an edge bounding the second bore 52 that is asymmetric to permit the bone anchoring element 1 to pivot at a larger angle at a first location where the recess 144 is located, than at another location of the edge relative to the longitudinal axis C as shown in FIG. 25. As depicted in FIG. 26, due to the flat surfaces 3a, 3b of the head 3, the bone anchoring element 1 is allowed to pivot only in a single plane. The single plane can be selected by rotating the bone anchoring element 1, the guiding member 400 and the seat member 140 together with respect to the receiving part 5.

Figure 27:
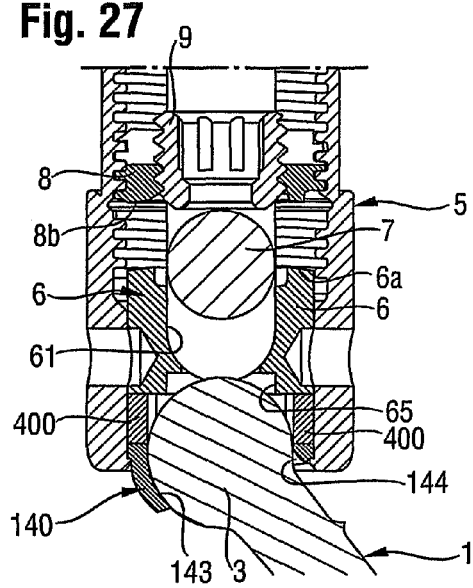
FIG. 27 shows a cross-sectional view of a step of mounting the rod to the bone anchoring device, the cross-section taken perpendicular to the rod axis.
Figure 28:
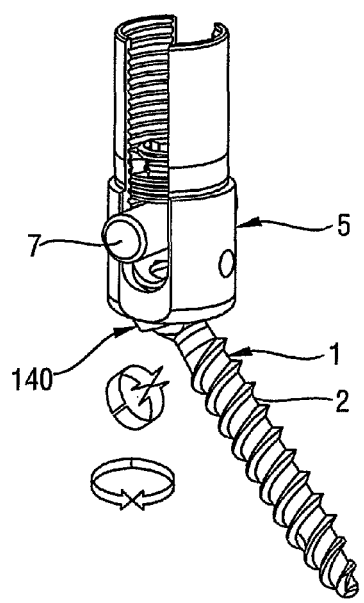
FIG. 28 shows a perspective view of the step of mounting the rod shown in FIG. 27.
Figure 29:
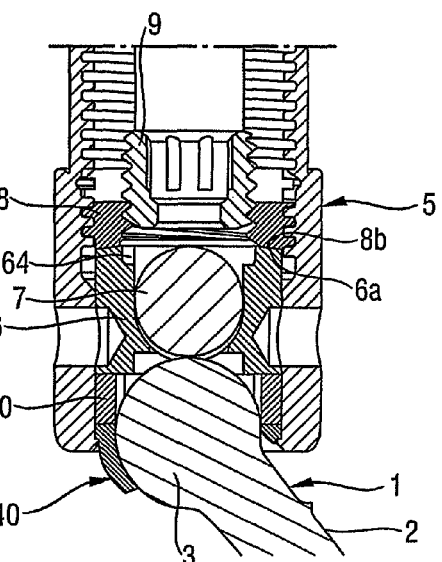
FIG. 29 shows a cross-sectional view of a step of locking the pivot plane of the bone anchoring device of the third embodiment, the cross-section taken perpendicular to the rod axis.
Figure 30:
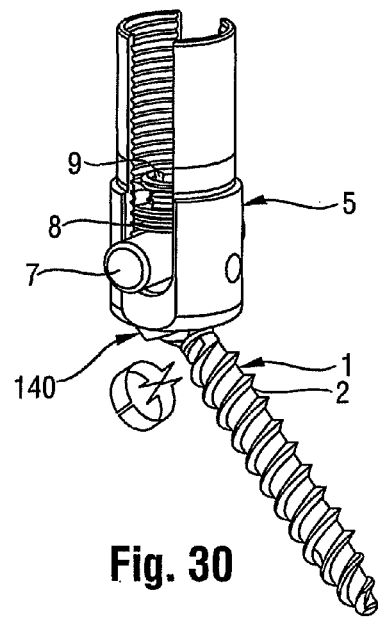
FIG. 30 shows a perspective view of the step of locking the pivot plane in FIG. 29.

Steps for using the bone anchoring device according to the third embodiment are shown in FIGS. 27 to 30. As shown in FIGS. 27 and 28, the orientation of the single pivot plane is selected when the bone anchoring element 1 has been inserted into the bone and the rod 7 is not yet inserted, by rotating the anchoring element 1 with the guiding member 400 and the seat member 140. Then, as shown in FIGS. 29 and 30, after insertion of the rod 7, the first locking element 8 is tightened and acts onto the pressure member 6, which in turn acts onto the guiding member 400 and the seat member 140 to fix the single pivot plane. The bone anchoring element 1 can then pivot in the single plane with a larger maximum pivot angle to the side that comprises the recess 144 as compared to the other side. By tightening the second locking element 9, the head 3 and the whole assembly is locked.

Modifications are possible also for the third embodiment. The design of the head 3 and the guiding member 4 can be modified like in the examples shown in FIGS. 14 to 17. Any connection between the head 3 of the bone anchoring element 1 and the guiding member 4 that limits pivoting of the bone anchoring element 1 to a single plane can be possible. In particular, the limitation can be achieved by a form-fit connection between the head 3 and the guiding member 4.

The pressure member 6 can be omitted. Instead of the pressure member 6, the locking device 10 has to be modified to act directly onto the guiding member 4.

The head 3 may have an additional engagement structure for engagement with a tool.

The orientation of the pivot plane can be selected before inserting the bone anchoring element 1 using a specific tool.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchoring device comprising:
a receiving part for receiving a rod, the receiving part having a longitudinal axis, a first bore coaxial with the longitudinal axis and a second bore;
an anchoring element having a first end for insertion into a bone and a second end positionable in the second bore, the second end including a head;
a guiding member configured to rotate in the first bore;
a locking device comprising a first locking element configured to act on the guiding member when the guiding member is in the first bore to fix the rotational position of the guiding member and a second locking element configured to act on the head when the head is in the second bore to fix the head;
wherein the head is guided by the guiding member and when the head and the guiding member are assembled in the receiving part a form-fit connection limits a movement of the anchoring element to a single plane;
wherein when the first locking element and the guiding member are assembled in the receiving part, the rotational position of the guiding member can be fixed in at least two or more positions within the receiving part; and
wherein when the rotational position of the guiding member is fixed by the first locking element, the anchoring element is movable relative to the receiving part in a limited angular range about the longitudinal axis, the angular range lying in the single plane.

2. The bone anchoring device of claim 1, wherein the receiving part comprises a U-shaped recess for receiving the rod, the U-shaped recess defining two open legs wherein an internal thread is provided at the open legs.

3. The bone anchoring device of claim 2, wherein the first locking element comprises an outer thread which is configured to cooperate with the internal thread at the open legs and wherein the first locking element comprises a coaxial bore comprising an internal thread configured to cooperate with an outer thread on the second locking element.

4. The bone anchoring device of claim 1, further comprising a pressure element having a recess shaped to receive the rod, the pressure element configured to be arranged between the guiding member and the locking device in the receiving part.

5. The bone anchoring device of claim 4, wherein the pressure element is configured to exert pressure on the guiding member but not on the head.

6. The bone anchoring device of claim 4, wherein the pressure element is substantially cylindrical and has a first end facing the locking device and a second end facing the head when the bone anchoring device is assembled and wherein the pressure element comprises a recess at the second end sized so that a portion of the head is capable of being accommodated therein without contacting the pressure element.

7. The bone anchoring device of claim 6, wherein the pressure element comprises a recess at its first end sized so that a portion of the second locking element is capable of extending therein without contacting the pressure element.

8. The bone anchoring device of claim 1, wherein an edge defining the second bore is asymmetric to permit the bone anchoring element to pivot at a larger angle relative to the longitudinal axis at a first location of the edge than at another location of the edge.

9. The bone anchoring device of claim 8, wherein the receiving part has a countersunk area at the edge defining the second bore.

10. The bone anchoring device of claim 1, wherein the head has a substantially spherical segment shape in which the rotational axis of the sphere extends perpendicular to the shank axis.

11. A method of using a bone anchoring device, the bone anchoring device comprising an anchoring element having a first end for insertion into a bone and a second end, the second end including a head; a receiving part for receiving a rod, the receiving part having a longitudinal axis, a first bore coaxial with the longitudinal axis and a second bore; a guiding member and a locking device comprising a first locking element and a second locking element; wherein the head and the guiding member are configured to have a form-fit connection that limits a movement of the anchoring element to a single plane; the method comprising:
  inserting the anchoring element into the receiving part;
  positioning the second end of the anchoring element in the second bore of the receiving part;
  inserting the guiding member into the first bore, wherein the guiding member is rotatable inside the first bore;
  assembling the head with the guiding member to form the form-fit connection between the head and the guiding member that limits the movement of the anchoring element to a single plane;
  inserting a rod into the first bore;
  assembling the first locking element and the guiding member in the receiving part such that the rotational position of the guiding member can be fixed in at least two or more positions within the receiving part;
  fixing the rotational position of the guiding member with the first locking member such that the anchoring element is movable relative to the receiving part in a limited angular range about the longitudinal axis, the angular range lying in the single plane; and
  fixing the head with the second locking member.

12. The bone anchoring device of claim 1, wherein when the head and the guiding member are assembled in the receiving part, a portion of the head projects out of the guiding member in a direction of the first locking member when the first locking member is in the receiving part.

13. The bone anchoring device of claim 1, further comprising a seat member having a bore and a seat for the head, the seat member configured to be assembled and mounted to the receiving part, wherein the seat member comprises an edge defining the bore of the seat member that is asymmetric to permit the bone anchoring element to pivot at a larger angle relative to the longitudinal axis at a first location of the edge than at another location of the edge.

14. The bone anchoring device of claim 1, wherein the seat member is configured to rotate in the second bore.

15. The bone anchoring device of claim 1, wherein the seat for the head is spherical.

16. The bone anchoring device of claim 1, wherein the seat member has a recess at its edge for a form-fit connection to the head.

\* \* \* \* \*